United States Patent [19]

Fontana

[11] Patent Number: 5,095,095
[45] Date of Patent: Mar. 10, 1992

[54] IMMUNOSUPPRESSANT FACTOR PROTEIN CAPABLE OF INHIBITING T-CELL MECHANISMS

[75] Inventor: Adriano Fontana, Zurich, Switzerland

[73] Assignee: Sandoz Ltd., Basel, Switzerland

[21] Appl. No.: 553,096

[22] Filed: Jul. 13, 1990

Related U.S. Application Data

[63] Continuation of Ser. No. 372,412, Jun. 27, 1989, abandoned, which is a continuation of Ser. No. 193,422, May 12, 1988, abandoned, which is a continuation of Ser. No. 708,692, Mar. 6, 1985, abandoned.

[51] Int. Cl.$^5$ .......................... C07K 3/00; C07K 13/00
[52] U.S. Cl. .................................... 530/350; 530/351; 530/827; 530/839
[58] Field of Search ............... 530/350, 300, 351, 827, 530/839

[56] References Cited

U.S. PATENT DOCUMENTS 4,683,135 7/1987 Pecht et al. .......................... 429/85
4,777,241 10/1988 Irikura et al. ...................... 530/350

OTHER PUBLICATIONS

Fontana et al. "Immunodeficiency in Glioblastoma Patients: Glioblastoma Cells Release Factors Inhibiting Interleukin-2-mediated Effects on T Cells" Neurology, Mar. 1984, vol. 34, No. 3, Suppl. 1, Abstract 4.

Primary Examiner—Nathan M. Nutter
Attorney, Agent, or Firm—Gerald D. Sharkin; Richard E. Vila

[57] ABSTRACT

An immunosuppressant factor derived from human glioblastoma cells.

3 Claims, 9 Drawing Sheets

IMMUNOSUPPRESSANT FACTOR PROTEIN CAPABLE OF INHIBITING T-CELL MECHANISMS

This is a continuation of application Ser. No. 07/372,412, filed June 27, 1989, now abandoned, which in turn is a continuation of application Ser. No. 07/193,422, filed May 12, 1988, now abandoned, which in turn is a continuation of application Ser. No. 06/708,692, filed Mar. 6, 1985, now abandoned.

The present invention is concerned with immunomodulatory substances.

It is more particularly concerned with an immunosuppressant factor capable of inhibiting T-cell mechanisms particularly those which are Interleukin 2 (IL-2) dependent.

The role of T-cells in cell-mediated immunity (e.g. by cooperation with B-lymphocytes) is well established. Substances which are capable of inhibiting T-cell mechanisms involved in the generation of antibodies or in lysis of target cells would be used to suppress or reduce the body's immune response. Such substances could thus be employed e.g. in connection with transplants to prevent rejection and also in connection with the treatment of diseases characterised by an auto-immune response in the body.

We have now found that cultured human glioblastoma cells secrete a factor that inhibits IL-2 dependent T-cell mechanisms. This factor has an inhibitory effect on IL-2 effects on thymocytes in the presence of lectins and on the induction of alloreactive cytotoxic T-cells in mixed lymphocyte cultures (MLC). IL 2 does not substitute for the inhibitor effect of the suppressor factor on the induction of the MLC. It further inhibits the growth of neuroblasts but not of fibroblasts. The glioblastoma cell derived suppressor factor was also found to inhibit the lectin response of human peripheral blood mononuclear cells isolated from blood donors. However, the inhibitory effect of the factor was maximal at sub-optimal lectin concentrations.

This factor can be obtained from the cystic fluid of glioblastoma tumors or from supernatant (SN) of cultured human glioblastoma cell lines and has an apparent approximate molecular weight of 97,000 and is also referred to herein as G-TsF.

The present invention will also be more particularly understood from the following description and reference to the accompanying drawings in which.

Cultured human glioblastoma cells are characterized by ultrastructural features, especially the presence of filaments, and by biochemical markers, such as glial fibrillary acidic protein (GFA) and S-100 protein (7, 14, 15). In addition human glioma cells express neuroectodermal antigens shared with melanomas and neuroblastomas (8), as well as Ia-like antigens and the common acute lymphoblastic leukemia antigen (CALLA), an antigen expressed on lymphoid cells from patients with the common form of acute lymphoblastic leukemia.

Two immunoregulatory mediators, a suppressor factor and a helper factor, were detected in the supernatant of glioblastoma cells. The helper factor shares the characteristics of macrophage-derived IL 1(1). The characterization of the factor as an IL 1-like mediator is based on the finding that the factor a) enhances the PHA(2)-induced thymocyte proliferation, b) exhibits no IL 2 activity, but c) augments the IL 2 production by mitogen-stimulated spleen cells, and d) has a m.w. of around 22,000. In this context it is of interest that mouse astrocytes stimulated with lipopolysaccharide and rat C$_6$ glioma cells secrete analogous IL 1-like factors in vitro (9, 18, 19). Furthermore, rat astrocytes have been shown to present antigen to T-lymphocytes, e.g. to activate myelin basic proteinspecific T lymphocyte lines (20). In addition, cultured rat astrocytes express Ia antigens upon interaction with T cells (20). The production of IL 1-like factors and the presentation of antigen by astrocytes may have a central role in the generation of immune responses in the brain. There is also recent evidence that the central nervous system is capable of mounting specific immune responses to antigens and tumor cells when introduced to the brain (21).

(1)=Interleukin 1
(2)=Phytohemagglutinin

Analogous to astrocytes, glioblastoma cells, which may represent transformed astrocyte precursor cells, do produce IL 1-like factors in vitro. The effect of the IL 1-like helper factor, however, is overriden by the presently described inhibitory factor also elaborated by the tumor cells. This factor inhibits the proliferative response of T cells to Con A (3) or to both PHA and IL 1/IL 2 standards. The factor also blocks the proliferation of an H-2-restricted, hapten-specific T cell line that normally grows in the presence of IL 2 and haptenated irradiated spleen cells. The glioblastoma-derived suppressor factor has no effect on IL 2 production by Con A-stimulated spleen cells and does not influence the growth of a thymoma cell line (EL 4 cells), which proliferates independently of IL 2. Taken together, these results indicate that the factor interferes with terminal events in the T cell activation cascade. The hypothesis that this glioblastoma-derived suppressor factor influences proliferative steps not necessarily involving direct IL 2 effects on T cells is based on the finding that the 97,000-m.w. factor does also inhibit the growth of neuroblasts, which grow independently of IL 2.

(3)=Concanavalin

Recently, the presence of immunosuppressive factors in the conditioned medium of various human tumor cells was investigated (22). Out of 12 different tumors (three melanoma, two sarcoma, and seven carcinoma) the SN of only three tumors produced greater than 30% inhibition of PHA-induced blastogenesis. However, as shown by dilution experiments the inhibitory effect was only visible up to a ¼ dilution of the SN; higher dilutions had no effect (22). When using the conditions to produce and to test the gliobalstoma SN, the SN of two neuroblastoma, a melanoma, and a rhabdomyosarcoma had no effect on responsiveness of thymocytes to Con A. This supports the assumption that among nonlymphoid tumors glioblastoma cells are at the present time unique for their capacity to release immunosuppressive factors in vivo and in vitro.

Depression of immune responsiveness has been documented in patients with glioblastoma (1-6). Impaired cell-mediated immunity in glioblastoma patients is indicated by depressed skin reactivity to common antigens, decreased ability to become sensitized to dinitrochlorobenzene, and decreased in vitro lymphocyte responsiveness to PHA or antigens. Factors released by the tumor cells may well account for the described T cell immune deficiency state. This idea is supported by the detection of imhibitory factors on T cell activation present in glioblastoma culture SN in vitro and in the cyst fluid of glioblastoma tumors in vivo. In addition the sera of glioblastoma patients contain a factor that inhibits the MLC and the PHA- and Con A-induced lymphocyte proliferation in vitro. After removal of the glioblastoma by neurosurgery, suppressor activity in the sera disappeared (1, 4).

Although it is well documented that in most glioblastoma patients, humoral immune responses to their tumors develop (23, 24), there is little evidence of significant cellular anti-tumor immune responses (25-27). In general, cytotoxic T cells have been implicated to contribute to the development of the cellular anti-tumor immune reactions (28, 29). The IL 2 dependency of the generation of CTL has been demonstrated by in vivo administration of highly purified IL 2 in concert with injections of tumor cells, which resulted in an augmented CTL and natural killer cell response in mice (30). The observed blocking of the generation of CTL by the glioblastoma cell-derived 97.000-m.w. factor according to the invention may account at least in part for inefficient immunosurvelliance against glioblastomas.

Impaired host immunocompetence may also emanate from lymphokine-induced production of mucopolysaccharide coats by glioblastoma cells that nonspecifically suppress the cellular immune response (31).

G-TsF is characterised by its activity spectrum as described above and in the examples hereinafter and its approximate molecular weight. Furthermore it is sensitive to tryptic proteolysis and had a peak of pI 4.6 on isoelectric focusing as hereinafter described. Purification can take place by various procedures such as conventionally used for the purification of cell factors. A particularly advantageous procedure involves successive chromatography of SN (optionally with pre-desalination) using first Blue-Affigel and then Hydroxyapatite followed by gel filtration e.g. on Ultro-gel AcA54, or on Ultro Pac TSK G 3000 SWG. Other absorbents which can be used include Phenyl-Sepharose, DEAE-cellulose and Heparin affigel. Other methods include the use of suitable antibodies.

In addition to its relevance for modulation of T cell activation the conditioned media of the glioblastoma is of interest for its neuroblast growth inhibitory factor (NGIF)-like activity. NGIF is released by fetal rat glioblasts and exerts suppressor activities on neuroblasts but not in fibroblasts (32, 33). In addition, this 75.000-m.w. factor possessed the activity to promote morphological differentiation of Neuro 2A cells as evidenced by the formation of neural processes (32, 33). In an analogous assay we also observed that the Sepharcryl S-200 glioblastoma fractions, which inhibited T cell responsiveness to IL 2 and the growth of neuroblasts, did induce neurite outgrowth, but had no effect on fibroblasts.

References referred to in the specification:

1. W. H. Brooks, et. al., Depressed cell-mediated immunity in patients with primary intracranial tumors. J. Exp. Med. 136:1631.
2. W. H. Brooks, et.al., Immune responses in patients with gliomas. Surg. Neurol. 2:419.
3. D. G. T. Thomas, et.al., Impaired cell-mediated immunity in human brain tumors. Lancet 11:1389.
4. H. F. Young, et.al., Inhibition of cell-mediated immunity in patients with brain tumors. Surg. Neurol. 5:19.
5. C. B. Menzies, et.al., Impaired thymus-derived lymphocyte function in patients with malignant brain tumor. Clin. Neurol. Neurosurg. 82:157.
6. T. L. Roszman, et.al., Immunobiology of primary intracranial tumors. Suppressor cell function and lectin-binding lymphocyte subpopulations in patients with cerebral tumors. Cancer 50:2173.
7. S. C. Diserens, et.al., Characterisation of an established human malignant glioma cell line: LN-18. Acta Neuropathol. 53:21.
8. S. N. Carrel, et.al., Expression of neuroectrodermal antigens common to melanomas, gliomas and neuroblastomas. Identification by monoclonal antimelanoma and antiglioma antibodies. Acta Neuropathol. 57:158.
9. A. Fontana, et.al., Production of prostaglandin E and an interleukin 1-like factor by cultured astrocytes and $C_6$glioma cells. J. Immunol. 129:2413.
10. H. P. Pircher, et.al., Restriction fine specificity of longterm, hapten-specific cytotoxic T-cell clones: Analysis with H-2K mutant mice and H-2K -specific monoclonal antibodies. Eur. J. Immunol.
11. J. C. Cerottini, et.al., Cell-mediated cytotoxicity, allograft rejection, and tumor immunity. Adv. Immunol. 18-67.

12. J. T. Kung, et.al., Suppression of in vitro cytotoxic response by macrophages due to induced arginase. J. Exp. Med. 146:665.
13. B. M. Stadler, et.al., Relationship of cell cycle to recovery of IL-2 activity from human mononuclear cells, human and mouse T cell line. J. Immunol. 127-1936.
14. A. Pactau, et.al., Glial fibrillary acidic protein and intermediate filaments in human glioma cells. Acta Neuropathol. 47:71.
15. A. Edstrom, et.al., Morpholigical alterations and increase of S-100 protein in cultured human glioma cells deprived of serum. Exp. Cell Res. 83:426.
16. S. Carrel, et.al., Expression of HLA-DR and common acute lymphol lymphoblastic leukemia antigens on glioma cells. Eur. J. Immunol. 12:354.
17. N. de Tribolet, et.al., In progress in Experimental Tumor Research, Vol. 27, Brain Tumor Biology. M. I. Rosenblum, et.al., eds. Karger, Basel.
18. A. Fontana, et.al., Biological and biochemical characterization of an interleukin-1 like factor from rat $C_6$glioma cells. Euro. J. Immunol. 13:685.
19. A. Fontana, et.al., Dual effect of glia maturation factor on astrocytes: differentiation and release of interleukin-1 like factors. J. Neuroimmunol. 5:216.
20. A. Fontana, et.al., Astrocytes present myelin basic protein to encephalitogenic T cell lines: Nature. 307: p. 273.
21. M. Hasek, et.al., Immunological tolerance and tumor allografts in the brain. Nature 186:68.
22. C. M. Renk, et.al., Inhibition of normal allogenic lymphocyte by a factor released from human tumor cells in culture. Cancer Immunol. Immunother. 11:7.
23. M. Pfreundschuh, et.al., Serologic analysis of cell surface antigens of malignant human brain tumors. Proc. Natl. Acad. Sci. U.S.A. 75:5122.
24. H. B. Coakham, et.al., Autologous humoral response to human gliomas and analysis of certain cell surface antigens: in vitro study with the use of interocytotoxicity and immune adherrence assay. JNCI 64:223.
25. N. L. Levy, 1978. Specificity of lymphocyte-mediated cytotoxicity in patients with primary intracranial tumors. J. Immunol. 121:903.
26. K. M. A. Sheik, et.al., Specific cellular immune responses in patients with gliomas. Cancer Res. 39:1733.
27. M. K. Gately, et.al., In vitro studies on the cell-mediated immune response to human brain tumors. Requirement for third-party stimulator lymphocytes in the induction of cell-mediated cytotoxic responses in allogenic cultured gliomas. JNCI 69:1245.
28. G. B. Millis, et.al., Generation of cytotoxic lymphocytes in syngeneic tumors by using co-stimulator (interleukin 2): in vivo activity. J. Immunol. 125:1904.
29. M. A. Cheever, et.al., Specific adoptive therapy of established leukemia with syngeneic lymphocyte sequentially immunized in vivo and in vitro and non-specifically expanded by culture with interleukin 2. J. Immunol. 126:1318.
30. S. H. Heffeneider, et.al., In vivo interleukin 2 administration augments the generation of alternative cytolytic T lymphocytes and resident natural killer cells. J. Immunol. 130:222.
31. S. J. Dick, et.al., Lymphoid cell-glioma cell interaction enhances cell coat production by human gliomas: novel suppressor mechanism. Science 220:739.
32. T. Kato, et.al., 1982. Inhibition of growth of mouse neuroblastoma cells by protein factor derived from rat glioblasts. Dev. Brain Res. 3:645.
33. Y. Sakazaki, et.al. 1983. Characterization and partial purification of neuroblastoma growth inhibitor factor from the culture medium of glioblasts. Brain Res. 262:125.

The following examples illustrate the invention. The following abbreviations are employed:

IL 1, Interleukin 1; IL 2, Interleukin 2; NGIF, neuroblast growth inhibition factor; SN, supernatant; GFA, glial fibrillary acidic protein; DMEM, Dulbecco's modified Eagle's medium; ConA, concanavalin A; 2-ME, 2-mercaptoethanol; $^3$H-Tdr.[$^3$H]thymidine; PHA, phytohemagglutinin; OVA cells, ovalbumin specific T-cell line; CTL, cytotoxic T-lymphocytes; MLC mixed lymphocyte culture; LPS, Lipopolysaccharide; AED, N-iodoacetyl-N-[5-sulfonic-1-naphthyl]ethylene diamine; CH, cycloheximide; FCS, fetal calf serum; G-TsF, Glioblastoma derived T cell suppressor factor.

EXAMPLE 1

Four human glioblastoma cell lines are established and maintained in mono-layer cultures by the method described in Diserens et. al., Acta Neuropathol. 53:21. Four cells lines used in the examples are designated Cl-18; Cl-229; 992 and 308 and were maintained for 72, 28, 8 and 16 months respectively.

Characterization of the glioblastoma cell lines revealed that cells from Cl-229, 308 and 992 expressed Ia-like antigens on their surface, cells from 308 and 992 were positive for glial fibrillary acidic protein (GFA), and cells from Cl-18, 308 and 992 expressed a neuroectodermal antigen identified by recently described monoclonal antibodies (Acta Neuropathol. 57:158 Carrell S., et. al.)

For production of SN the glioblastoma cells were plated at $1 \times 10^4$ to $1 \times 10^6$ cells/well (2.4×1.7 cm; Linbro Scientific) in culture medium consisting of Dulbecco's modified Eagle's medium (DMEM), 10% fetal calf serum (FCS), and 300 ug/ml L-glutamine. Twenty-four hours after plating the glioblastoma cells, the medium was replaced with 0.5 ml culture medium. The SN were collected 1 to 5 days later, centrifuged (2000×G. 10 min) and ultrafiltrated by using a microparticle system with YMB membrane (MPS. 1, Amicon). The material deposited after centrifugation (1500×G. 15 min) on the membrane (m.w.>10.000), was resuspended in RPMI 1640 to give the original volume and passed through 0.45-μm filters.

EXAMPLE 2

Selection of Absorbents

The following adsorbents were tested: Bio-Gel HTP (hydroxyapatite), Blue-Affigel, Heparin-Affigel (Bio-Rad, Ricmond, CA); Phenyl-Sepharose, ConA-Sepharose, Protein A-Sepharose (Pharmacia, Uppsala, Sweden); DEAE-Cellulose, CM-Cellulose (Serva, Heidelberg, Germany). Each adsorbent was equilibrated in the appropriate adsorption buffer listed in Table I and the slurry was transferred to a disposable 5 ml-plastic column (Isolab, Akron, Ohio) to give 0.2 ml of settled volume. After closing the column at the bottom, 0.5 ml of a G-TsF standard (activity 100 units) was added and the slurry was kept in suspension overnight at 4° C. on a rotating turn table. The column was then drained, and the effluent was desalted and assayed for protein content [Lowry et. al., J. Biol. Chem; 193: 265; 1951] and for G-TsF activity using the Neuro 2A assay (see below). The adsorbent was resuspended in the appropriate desorption buffer (Table IV), kept in suspension for 2 hours at 4° C., drained and G-TsF and protein content in the column effluent were determined as above. Overall recoveries were at least 80%.

EXAMPLE 3

Purification of G-TsF (see Table V)

Figure 9:
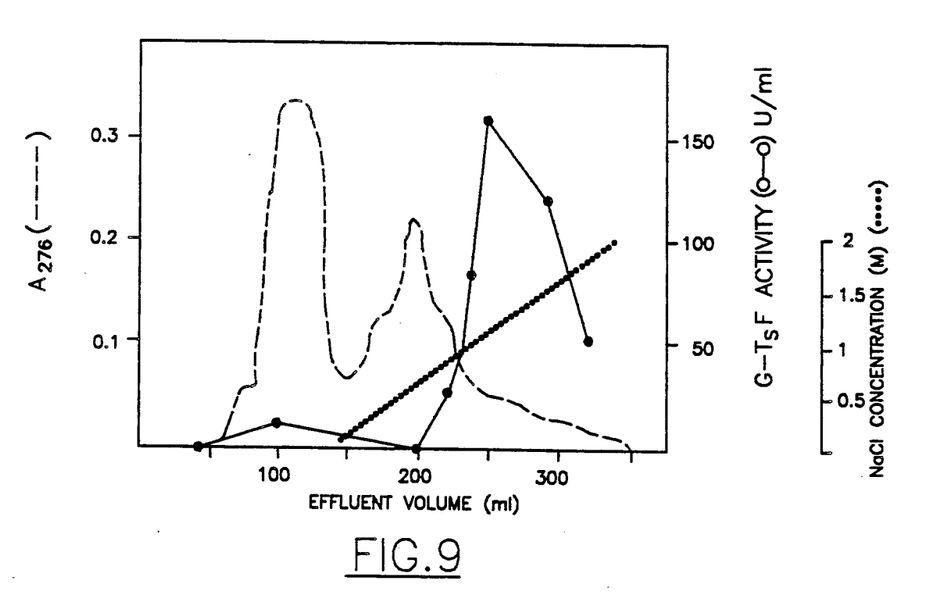
FIG. 9 illustrates G-TsF activity and column fraction.
Figure 10:
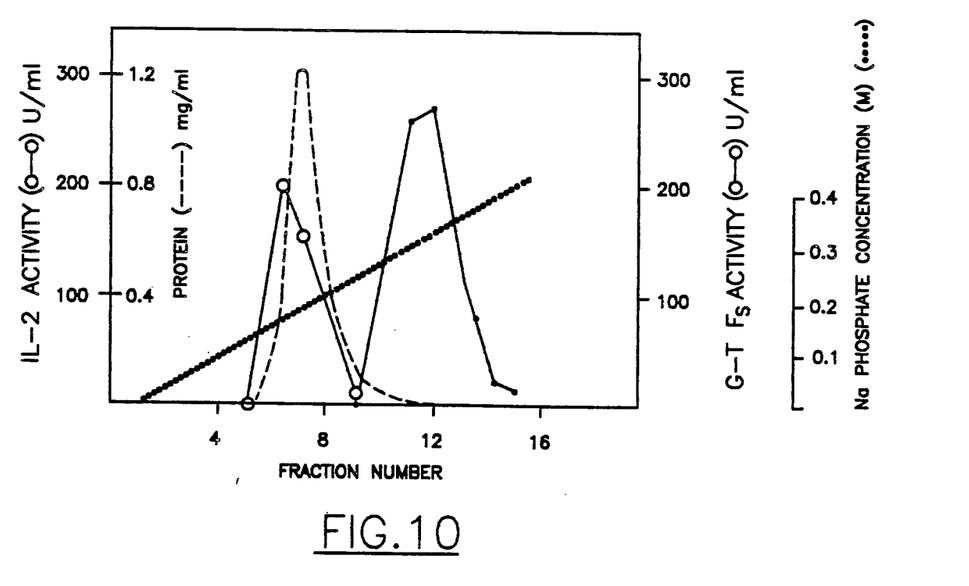
FIG. 10 illustrates G-TsF activity and IL-1 activity of column fractions.

The 308 SN (150 ml) was concentrated 6-fold by ultrafiltration through a 43 mm YM10 membrane (Amicon, Danvers, Mass.) and then rediluted to a volume of 50 ml by adding 10 mM Tris-HCL, pH 7.5. The concentrate was applied at 4° C. to a column of Blue-Affigel (1.6×35 cm; 70 ml bed volume) at a flow rate of 48 ml/hr. The column was eluted with a linear gradient (280 ml) of 2M NaCl in 10 mM Tris-HCl, pH 7.5. The fractions containing G-TsF activity as determined on ConA stimulated thymocytes (70 ml; 1.0–1.5M NaCl) (cf. FIG. 9) were pooled, diluted with 70 ml of 10 mM Na phosphate, pH 7.5, and applied at room temperature to a column of hydroxyapatite (Bio-Gel HTP; 0.8×28 cm; 14 ml) at a flow rate of 12 ml/hr. From here on, all fractions were collected in siliconized plastic tubes [Maniatis et. al., Molecular cloning. Cold Spring Harbor Laboratory, New York, p. 437]. The column was eluted with a linear gradient (105 ml) consisting of 10 mM Na phosphate, pH 7.5, 0.15M NaCl (start buffer) and 0.5M Na phosphate, pH 7.5 (limit buffer). Each of the fractions (7.5 ml) containing G-TsF activity (cf. FIG. 10) (0.25–0.35 Na phosphate) was applied in a separate run to a column of Ultrogel AcA 54 (LKB, Bromma, Sweden) (1.6×88 cm; 176 ml) which had been equilibrated at 4° C. in 10 mM Tris-HCl, pH 7.5, 0, 15M NaCl and calibrated with Blue Dextran (v), bovine serum albumin (BSA), ovalbumin, and cytochrome c (Cyc). The column was eluted at 20 ml/hr with the same buffer, and the fractions containing G-TsF activity were pooled and stored at −20° C. Alternatively the fractions from the HTP column containing G-TsF activity were concentrated by ultrafiltration through a YM10 membrane and further purified on a preparative HPLC gel filtration column (TSK 3000 SWG LKB-Bromma). Protein concentrations were determined with the amidoblack assay [Schaffner, Weissmann Anal Biochem 56:514, 1973] or spectrophotometrically and salt concentration by conductivity. IL-1 activity was measured using PHA stimulated thymocytes.

EXAMPLE 4

Isoelectric Focusing

Figure 11:
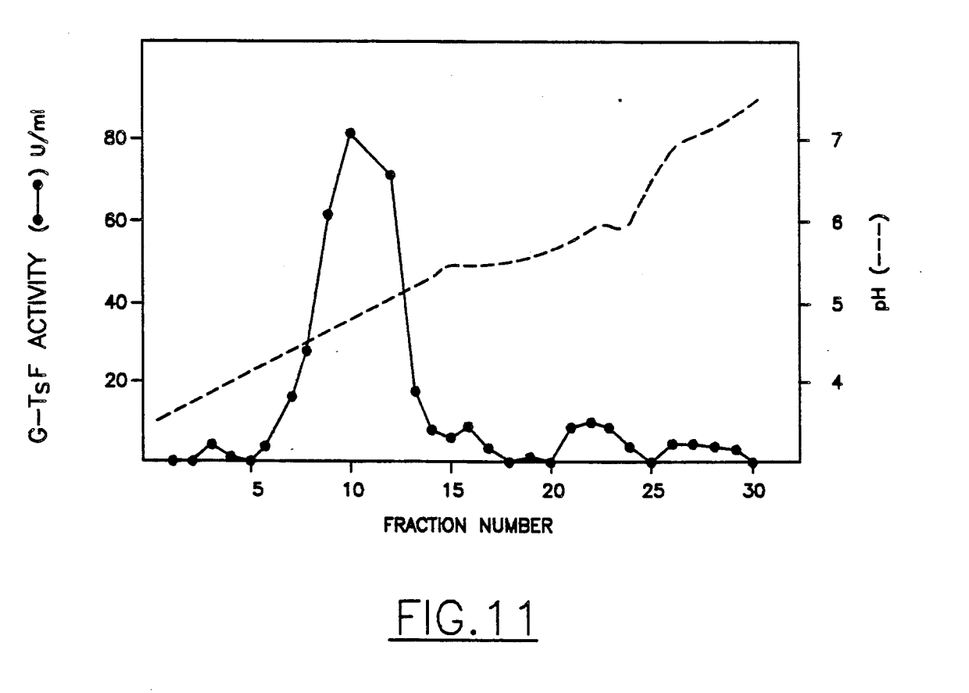
FIG. 11 is a graph showing the isoelectric point of the major peak of activity obtained from fractionation of the 308 SN.

A sample of the G-TsF (60 ml) obtained after Example 3 (Table V step 4) was concentrated by ultrafiltration through an Amicon YM10 membrane for partial removal of salt which interferes with formation of the pH gradient. The G-TsF was then mixed with 85 ml Ultrodex (4 g preswollen in 100 ml H$_2$O), 2.5 ml Ampholines pH 3.5–5, and 2.5 ml Ampholines pH 5–8 (all from LKB) at 10 W and 1'2000 V for 16 hr. After the run, the gel was sliced into 30 fractions, and their pH was determined with a surface glass electrode. Each fraction was transferred to a disposal 5 ml-plastic column, and the proteins were eluted with 2 ml of 10 mM Tris-HCl, pH 7.5, 0.15M NaCl, desalted in Sephadex G50 columns to remove Ampholines, and assayed for G-TsF activity using the ConA-thymocyte assay (see below). A peak was determined at P$^I$ 4.6(cf. FIG. 11).

EXAMPLE 5

Tryptic Proteolysis

Samples of G-TsF (0.2 ml) obtained after Example 3 (Table V step 3) were incubated for 1 hr at 370° C. with 8 μg trypsin (Worthington; treated with L-1-tosylamido-phenylethyl chloromethyl ketone), added either at the beginning or—as a control—at the end of the incubation period. Additional samples were incubated with Sepharose-bound trypsin (0.2 ml settled gel; Worthington) or with an equivalent amount of RNase A coupled to Affigel 10 (Bio Rad). The reactions were stopped by using the desalting protocol described above and then testing for G-TsF activity in the ConA-thymocyte assay. The results are shown in Table VI. Parallel incubations with 125 I labelled factor indicated a loss of protein by non-specific adsorption to the Affigel 10, thus explaining the low recovery of G-TsF activity from the RNAase column

EXAMPLE 6

Thymocyte Proliferation Assay

The effect of glioblastoma SN on the thymocyte proliferative response to concanavalin A (Con A) was tested in the following way. Samples of 50 μl of SN at various dilutions were added to 6×10$^5$ thymocytes from C$_3$H/HeJ mice: thymocytes were suspended in 150 ul of RPMI 1640 medium supplemented with 300 μg/ml L-glutamine. 1×10$^{-5}$M 2-mercaptoethanol (2-ME). and 5% FCS in flat-bottomed microtiter plates and incubated for 72 hours in the presence of Con A (1 μg/well). Sixteen hours before harvest 0.5 μCi of $^3$H-Tdr. (5.0 Ci/mmol) was added per well.

Figure 1A:
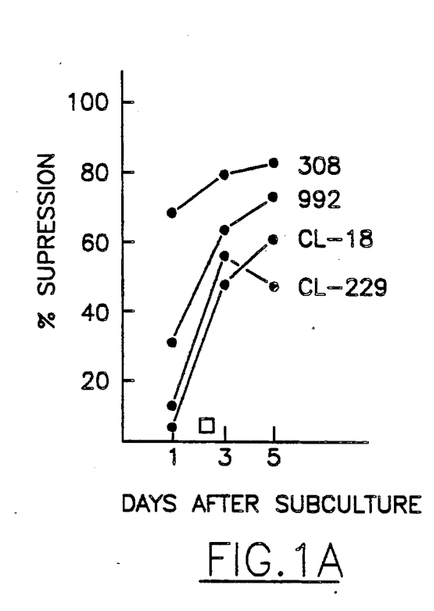
FIG. 1A is a graph illustrating the percent suppression of the thymocyte proliferative response by glioblastoma SN on four cell lines as a function of days after subculturing.
Figure 1B:
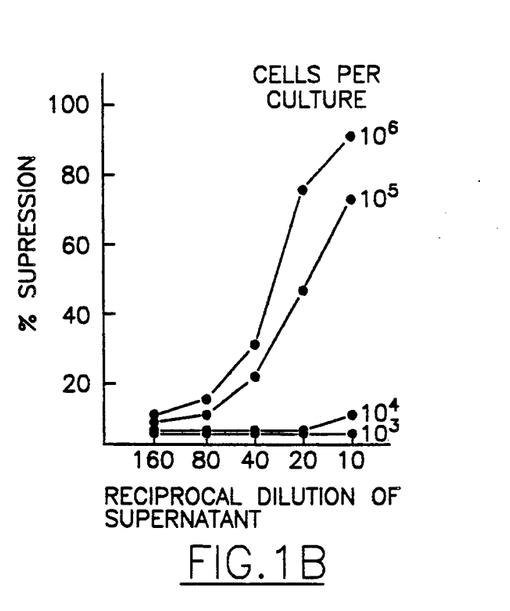
FIG. 1B is a graph illustrating the percent suppression of the thymocyte proliferative response by glioblastoma SN on four cell lines as a function of cell density.

The results are shown in FIGS. 1A and B as percent suppression compared with the Con A response of thymocytes treated with a medium control.

For standardization purposes % suppression can be plotted to give a standard curve from which conversion may be made to units of G-TsF activity.

In FIG. 1A and SN of the four glioblastoma cell lines used were harvested after 1, 3 and 5 days and tested at a final dilution of 1/10 on the thymocytes. In FIG. 1B the testing took place on SN of 308 cells harvested after culture for 5 days at different seeding densities and final dilutions. In the absence of glioblastoma SN or medium control the background count was 483±229 and the Con A response 76.797±6.631 cpm.

The magnitude of inhibitory potency of the SN can be seen to be dependent on time of culture and cell density.

In selected experiments on metabolic inhibition using 308 cells the production of SN was performed with irradiated (2000 R) or mitomycin C-treated (50 μg/ml, 30 min. 37° C.) glioblastoma cells. Alternatively cycloheximide (10$^{-5}$M) was added to glioblastoma cells at the beginning of the 72-hour culture; cycloheximide was also added to control SN collected after 72 hours. These SN were ultrafiltrated three times before testing to remove CH.

Figure 2:
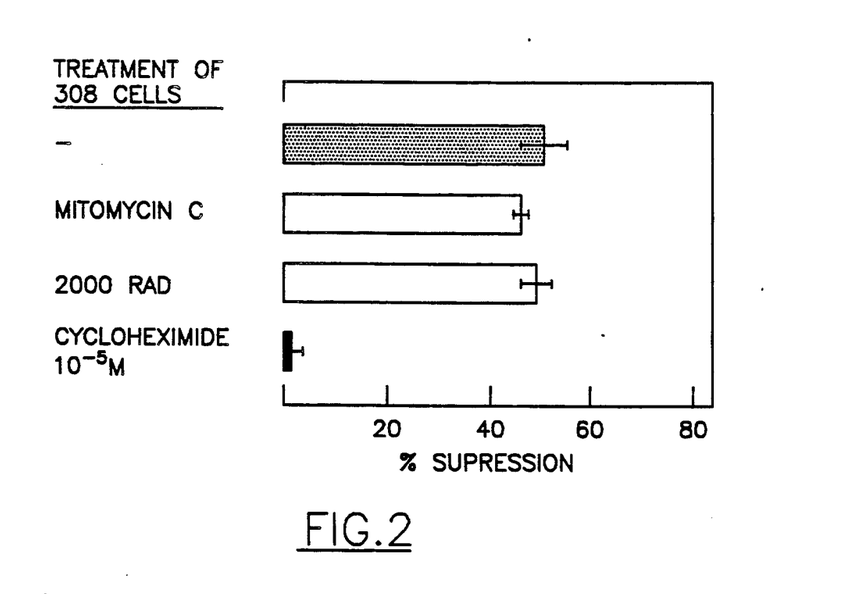
FIG. 2 is a graph illustrating the percent suppression of the thymocyte proliferative response of SN obtained from 308 cells exposed to various metabolic inhibitors.

The results of these experiments are summarised in FIG. 2, where the SN of 10$^6$ cells cultured over 5 days were employed. As a CH control the SN of CH treated 308 cells and of 308 SN supplemented with CH after collection were ultrafiltrated.

In a further control, experiments were carried out on four established human tumor cell lines unrelated to glioblastoma cells. These results are summarised in Table 1.

TABLE I

Effects of SN from various tumor cell lines on lymphocyte blastogenesis

| Type of Malignancy[a] | Designation | Con A Response[b] (cpm ± SD) | % Suppression |
|---|---|---|---|
| Neuroblastoma | SR.N.SH | 52.123 ± 1.817 | 6.0 |
| Neuroblastoma | IMR.32 | 50.041 ± 2.751 | 9.8 |
| Melamoma | Me.43 | 58.382 ± 447 | 0 |
| Rhabdomyosarcoma | RD | 51.720 ± 904 | 6.8 |

[a]Tumor cells were cultured at a seeding density of $10^6$ cells/ml for 5 days.
[b]In the presence of Con A, thymocytes were incubated with 1/10 dilution of tumor cell SN or a control culture medium for the tumor cell SN. In the presence of medium control the background count of thymocytes was 432 ± 112 and the Con A response was 55441 ± 4817.

It will be noted that the release of immunosuppressive factors does not appear to be a general property of cultured tumor cells.

Analysis of the L-arginine content in 308 SN revealed that inhibition is not due to arginine degradation in the medium by an arginase release by 308 cells. Furthermore, the 308-mediated inhibition could not be explained by the production of interferon as no antiviral activity was detected in 308 SN.

EXAMPLE 7

Effect of Glioblastoma SN on B Lymphocytes and Non-lymphoid Cells

Mouse fibroblasts (A9, 3T3, LS cell lines) were cultured in DMEM supplemented with L-glutamine (300 ug/ml) and 10% FCS: mouse neuroblasts (Neuro 2A, NB4, 1A3 cell lines) were plated in Earle's minimum essential medium with 10% FCS. L-glutamine (300 ug/ml), and 1% nonessential amino acids (100x). Fibroblasts and neuroblasts ($10^4$ cells/well) were incubated in 0.2 ml of medium for 72 hours. For the final 6 hours, the cells were pulsed with 1.2 $\mu$Ci of $^3$H-Tdr. Thereafter, the medium was aspirated from each well, replaced with trypsin-EDTA. and incubated (37° C., 10 min). Finally, the cells were harvested with the use of an automated harvester.

The data in Table II indicate that when compared with its effect on thymocytes, the 308 SN was less inhibitory on B cell proliferation: the percentage of inhibition of the LPS-induced stimulation of spleen cells was 29%, whereas the corresponding value for the myeloma cell line X63-Ag8 was 21%.

There was no difference in thymidine uptake between fibroblast cultures containing 308 SN and those being supplemented with a medium control. This was true for all three fibroblast cell lines tested. In contrast, the gliobalstoma SN singificantly suppressed the growth of the two neuroblast cell lines as measured by the uptake of $^3$H-Tdr (FIG. 3, Table II) and by counting the number of cells at termination of the 72 hr cultures. Twenty-four, 48 and 72 hr after culturing $1\times10^4$ Neuro 2A cells/well, the cell numbers $\times 10^4$/well of quadruplicate cultures were in the presence of the 308 SN:0.98±0.17 (24 hr), 1.8±0.36 (48 hr), and 4.3±0.44 (72 hr), whereas the corresponding values for the medium controls were 0.88±0.05, 2.55±0.06, and 6.08±0.40, respectively.

TABLE II

Effect of 308 SN on lymphoid and nonlymphoid cells

| Cell Type | Description or Strain | Stimulant | $^3$H-Tdr Uptake (cpm) Medium control | $^3$H-Tdr Uptake (cpm) 308 SN[a] | % Suppression |
|---|---|---|---|---|---|
| Thymocytes | C3H/HeJ | Con A | 66.709 ± 3.104 | 8.323 ± 235 | 88 |
| T cell lymphoma | EL-4 | — | 137.960 ± 25.173 | 164.487 ± 6.253 | 0 |
| Spleen cells | DBA | LPS[b] | 72.442 ± 3.886 | 50.990 ± 2.184 | 29 |
| Myeloma cells | X63-Ag8[b] | — | 117.090 ± 2.597 | 92.580 ± 6.351 | 21 |
| Neuroblasts[c] | NB41A3 | — | 48.073 ± 1.756 | 15.504 ± 833 | 68 |
| Neuroblasts | Neuro 2A | — | 250.807 ± 19.700 | 62.408 ± 6.108 | 76 |
| Fibroblasts[c] | A9 | — | 78.591 ± 11.029 | 78.323 ± 10.444 | 0 |
| Fibroblasts | 3T3 | — | 117.316 ± 8.484 | 117.011 ± 4.026 | 0 |
| Fibroblasts | L929 | — | 84.395 ± 6.189 | 92.391 ± 5.674 | 0 |

[a]All assays were performed with the same 308 SN added to give a final dilution of 1/10.
[b]After lysis of erythrocytes 6 × $10^5$ spleen cells were stimulated with lipopolysaccharide (LPS.E.coli 0127 B8, Difco Lab.). The mouse X63-Ag8 myeloma cells were cultured at $10^4$ cells/well in DMEM supplemented with 10% FCS.
[c]See legend of FIG. 3.

Figure 3:
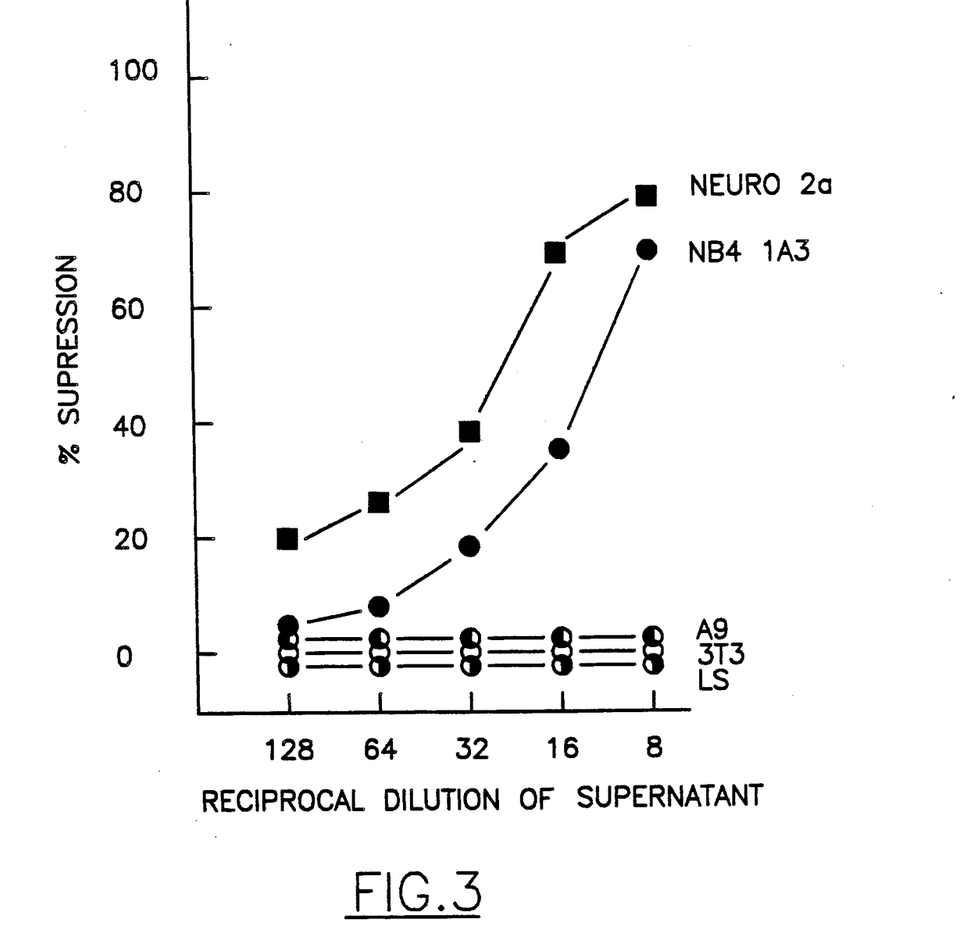
FIG. 3 is a graph illustrating thymidine uptake by three fibroblast cell lines exposed to varying amounts of glioblastoma SN.

In FIG. 3 the SN of $10^6$ glioblastoma cells (308) cultured for 5 days were employed together with a medium control.

EXAMPLE 8

Mechanisms of Glioblastoma SN-induced Inhibition of T-cell Activation

Thymocytes were treated with 308 SN (final dilution of 1/10) in the presence of PHA (0.5 ug/well) and various dilutions (1/10 in 1/160) of IL 1 or IL 2. In the absence of interleukins the background count was 209±84 and the PHA response was 3074±425.

The results are summarised in Table III.

TABLE III

Effect of 308 SN on thymocytes stimulated with PHA and various doses of IL 1 or IL 2

| Stimulant[a] | | $^3$H-Tdr Uptake (cpm) Medium control | $^3$H-Tdr Uptake (cpm) 308 SN | % Suppression |
|---|---|---|---|---|
| PHA + IL 1[b] | 1/10 | 76.342 ± 5.978 | 12.104 ± 618 | 84.2 |
| | 1/20 | 69.831 ± 5.150 | 13.423 ± 212 | 81.8 |
| | 1/40 | 42.143 ± 1.706 | 9.061 ± 842 | 78.5 |
| | 1/80 | 18.407 ± 128 | 2.648 ± 221 | 85.7 |
| PHA + IL 2[b] | 1/10 | 84.457 ± 3.621 | 13.551 ± 817 | 84.0 |
| | 1/20 | 84.882 ± 4.185 | 15.492 ± 1.005 | 81.8 |
| | 1/40 | 76.537 ± 2.404 | 11.250 ± 1.423 | 85.4 |
| | 1/80 | 43.244 ± 1.753 | 5.973 ± 175 | 86.2 |

TABLE III-continued

Effect of 308 SN on thymocytes stimulated with PHA and various doses of IL 1 or IL 2

| Stimulant[a] | | $^3$H-Tdr Uptake (cpm) | | % |
|---|---|---|---|---|
| | | Medium control | 308 SN | Suppression |
| | 1/160 | 26.505 ± 1.044 | 3.182 ± 3.279 | 88.0 |

[a]Thymocytes were treated with 308 SN (final dilution of 1/10) in the presence of PHA (0.5 µg/well) and various dilutions (1/10 to 1/160) of IL 1 or IL 2. In the absence of interleukins the background count was 209 ± 84 and the PHA response was 3074 ± 425.

[b]The IL 1 preparation used was prepared from LPS-stimulated peritoneal cells of BALB/c mice; the IL 2 was prepared by stimulation of BALB/c spleen cells with Con A-Sepharose as described previously (17).

These results show that inhibition of the Con A response of thymocytes apparently results from influences on late events of the T cell activation cascade, because the 308 SN inhibited the proliferative response of thymocytes stimulated with PHA in the presence of IL 1 or IL 2. The degree of 308 SN-induced suppression of proliferation was similar at various concentrations of IL 1 or IL 2 employed.

EXAMPLE 9

Effect of SN-308 on Cloned T-cell Lines

Proliferation of H-2$^b$-restricted hapten (N-iodoacetyl-N-(5-sulfonic-1-naphthyl) ethylene diamine [AED])-specific cloned cytotoxic T-cells (CTL) (10) was assessed in culture medium consisting of Iscove's modified DMEM supplemented with 10% FCS, $1 \times 10^5$M 2-ME, antibiotics and 10% 10% (v/v) of a 24-hr spleen cell Con A SN (IL 2 SN). The CTL ($10^4$/well) were cultured alone or together with $10^6$ irradiated (2000 rad) haptenated spleen cells (H-2$^b$) as stimulators. Various dilutions of SN of 308 glioblastoma cells or of a control medium were added to the mixture of the CTL and stimulators cultured in culture medium for 72 hr. Sixteen hours before harvest, each well was pulsed with 1.2 µCi of $^3$H-Tdr.

Figure 4:
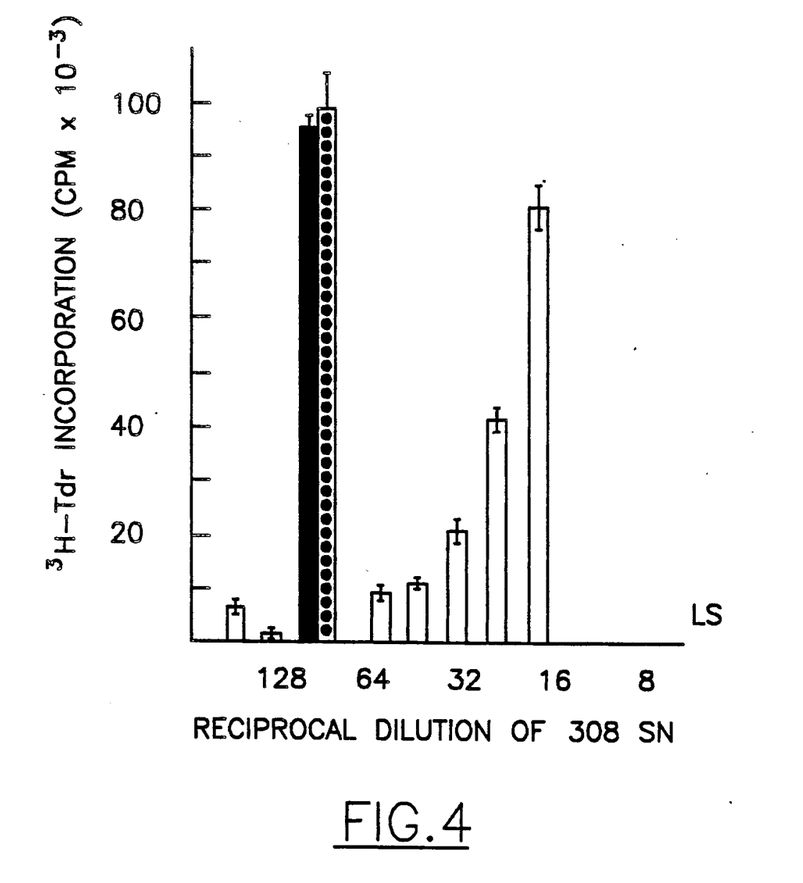
FIG. 4 is a graph illustrating incorporation of $^3$H-Tdr by hapten-specific CTL cells, cultured alone and with stimulaters, and exposed to varying dilutions of glioblastoma SN.
Figure 5A:
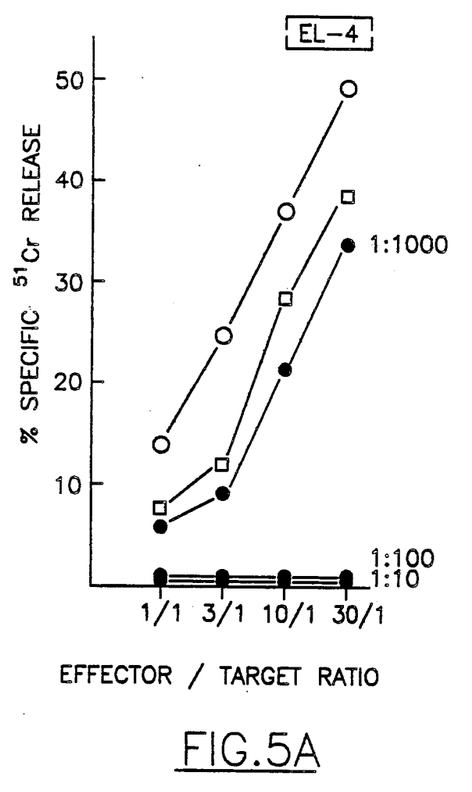
FIG. 5A is a graph illustrating the release of $^{51}$Cr in EL-4 target cells cultured in various media and exposed to various concentrations of 308 SN.
Figure 5B:
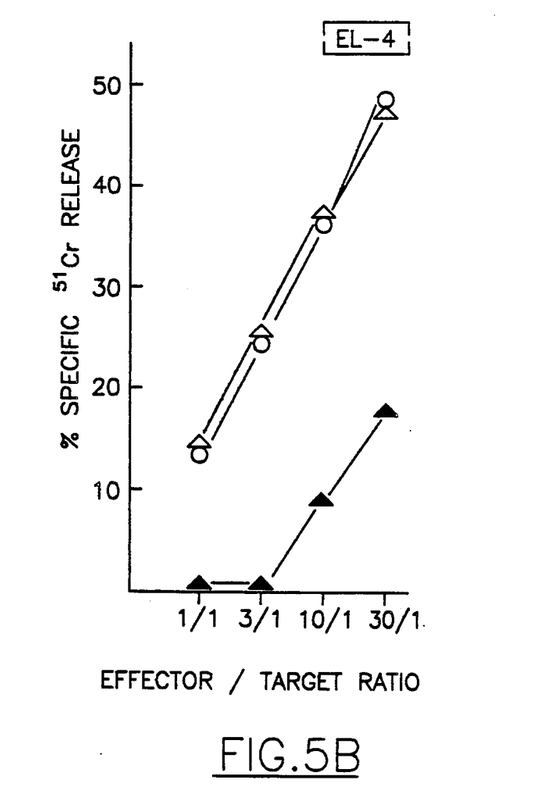
FIG. 5B is a graph illustrating the release of $^{51}$Cr in EL-4 target cells exposed to various column fractions known to inhibit or have no effect on proliferation of OVA T cells.
Figure 5C:
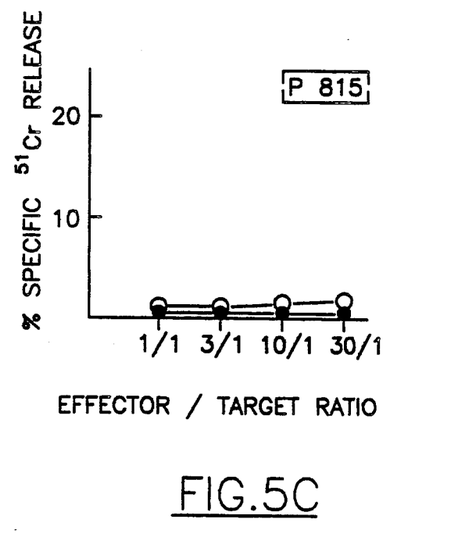
FIG. 5C is a graph illustrating the release of $^{51}$Cr in P815 target cells exposed to 308 SN.
Figure 5D:
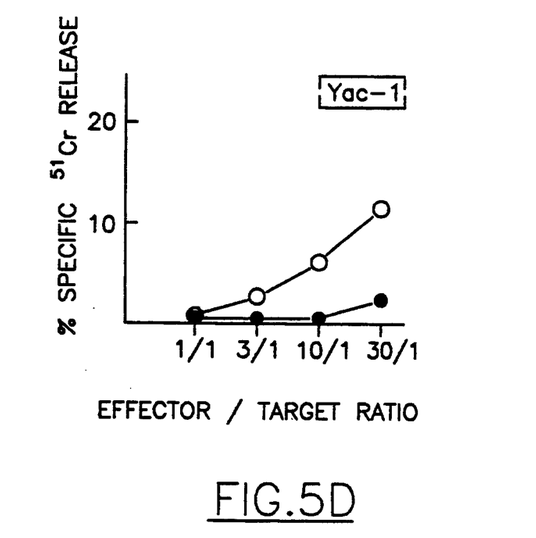
FIG. 5D is a graph illustrating the release of $^{51}$Cr in Yac-1 target cells exposed to 308 SN.

The results are shown in FIG. 4. Hapten-specific cloned CTL were cultured (at $10^4$ cells) alone (R) or together with $10^6$ irradiated (2000 rad) AED-haptenated spleen cells as stimulators (S) (black bar). Various dilutions (⅛ to 1/128) of 308 glioblastoma SN or a ⅛ dilution of control medium (   ) were added to the mixture of CTL and cultured for 72 hr. Data are given as counts per minute of $^3$H-Tdr incorporation. FIG. 4 shows that cells of an H-2-restricted, hapten-specific T-cell line proliferated in the presence of IL 2 and haptenated, irradiated spleen cells as stimulator cells. This proliferation was completely blocked by adding the glioblastoma-produced factor.

From the experiments outlined above, the inhibition of T cell growth by glioblastoma cell-derived factors could be due to their direct interference with IL 2-triggered events leading to T cell proliferation. This possibility is supported further by the finding that the 308 SN had no effect on the growth of a thymoma cell line that grows independently of IL 2 (Table II).

EXAMPLE 10

The release of analogous inhibitory factors by the glioblastoma cells in vivo was demonstrated by testing the ultrafiltrated cyst fluid of the patient from whom the 308 cells originated. The cyst fluid (final dilution 1/20), ultrafiltrated on YMB membranes, induced a 28% inhibition of the IL 2-induced proliferation of OVA T cells, whereas 12 control sera had no effect.

EXAMPLE 11

Effect of Glioblastoma SN on the Induction of Cytotoxic T-Cells

Anti-H-2$^b$-specific CTL were induced by stimulation of $12 \times 10^6$ B10.D2 (H-2$^d$) spleen cells with $30 \times 10^6$ irradiated (2000 R) C57B1/6 (H-2$^b$) stimulator spleen cells in 6 ml Iscove's modified DMEM containing 10% FCS. $1 \times 10^{-5}$M 2-ME, and antibiotics (mixed lymphocyte culture (MLC) medium). After 6 days the specific cytotoxic activity of the CTL was tested in a 3-hr $^{51}$Cr-release assay in 0.2 ml cultures containing $10^4$ $^{51}$Cr-labelled target cells (EL-4 (H-2$^b$), P815 (H-2$^d$). Yac-1 (H-2$^d$)) at different target ratios as described in 11. The cytotoxic effect of the cells cultured over 6 days in MLC medium was compared with the effects of cells cultured in MLC medium being supplemented with medium control or 308 SN.

The results are summarized in FIGS. 5A–D. Legend FIG. 5. The cytotoxic effect of the cells cultured over 6 days in MLC medium (◯—◯) was compared with the effects of cells cultured in MLC medium being supplemented with a) medium control (final dilution 1/10) (□—□), b) 308 SN (   —   ) diluted 1/10 (A-D). 1/100 or 1/1000 (A) or with c) Sephacryl S-200 column fractions that were known to inhibit (   —   ) or to have no effect (△—△) on the IL 2-dependent proliferation of OVA T cells. The fractions to be assayed were concentrated 10× on YMB membranes, and the concentrated fractions were added to MLC medium to give a final dilution of 1/10. Results are given as percent specific $^{51}$Cr release (see Reference 11). Test duration 3 hr. Mean values of three samples.

The data indicate a 308 SN induced inhibition of the generation of CTL. The inhibitory effect is mediated by factors with an apparent molecular weight of 97,000.

(The preparation and testing of Sephacryl S-200 column fractions is described below).

Figure 6A:
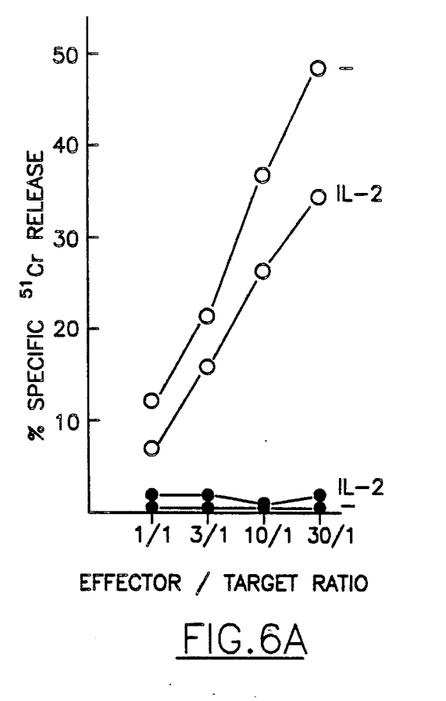
FIG. 6A is a graph illustrating the release of $^{51}$Cr by EL-4 cells exposed to both 308 SN and IL-2.
Figure 6B:
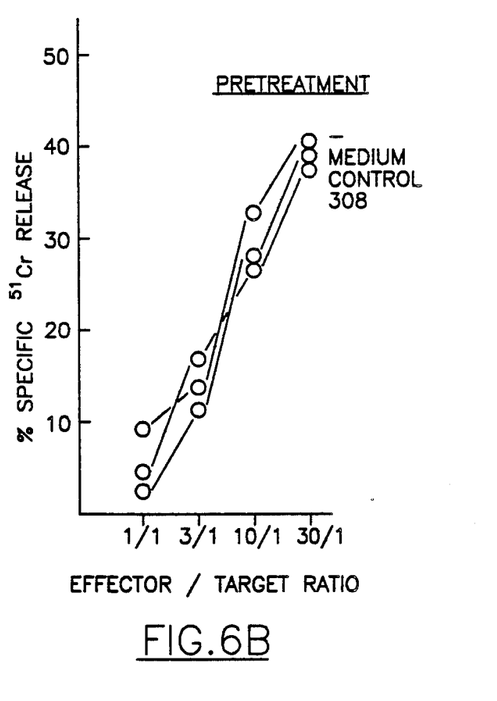
FIG. 6B is a graph illustrating the release of $^{51}$Cr by EL-4 cells preincubated in 308 SN.

As shown in FIG. 6 the addition of IL 2 together with the 308 SN factor did not restore the generation of CTL. A 2-hr preincubation of mature CTL with 308 SN had no influence on the function of CTL on their targets.

In FIG. 6 A during the entire culture period of 6 days, IL 2 (final concentration of 10% Con A SN) was present in MLC treated with 308 SN (1/10 diluted) (   —   ) or medium control (◯—◯). After 6 days the CTL activity was tested on EL-4 cells. In B. before testing on EL-4 cells, CTL generated over 6 days in culture medium were preincubated for 2 hr in medium control or 308 SN (¼ diluted).

EXAMPLE 12

Biochemical Characterisation of the Glioblastoma SN

The 308 glioblastoma SN obtained from 308 cells cultured in serum free conditions over 96 hr was concentrated 30-fold by ultrafiltration on YM-10 (Amicon) membrane, and 1.5 ml of concentrated SN was applied on a Sephacryl S-200 (column size 2.5×85 cm) at 4° C. as described (9). The eluate collected in 2.5 ml fractions was monitored for adsorbance at 280 nm and was tested on fibroblasts (L 929) and neuroblasts (Neuro 2 A) as described above. In addition the fractions were tested on OVA cells in the presence of IL2 and on thymocytes stimulated with PHA. The column, in a parallel run, was calibrated with δ-globulin (δ-Glob. m.w. 150.000). bovine serum albumin (BSA. m.w. 67.000), ovalbumin (OVA, m.w. 45.000), α-chymotrypsinogen (CHY. m.w. 25.000), and cytochrome c (CYT C. m.w. 12.400).

Figure 7:
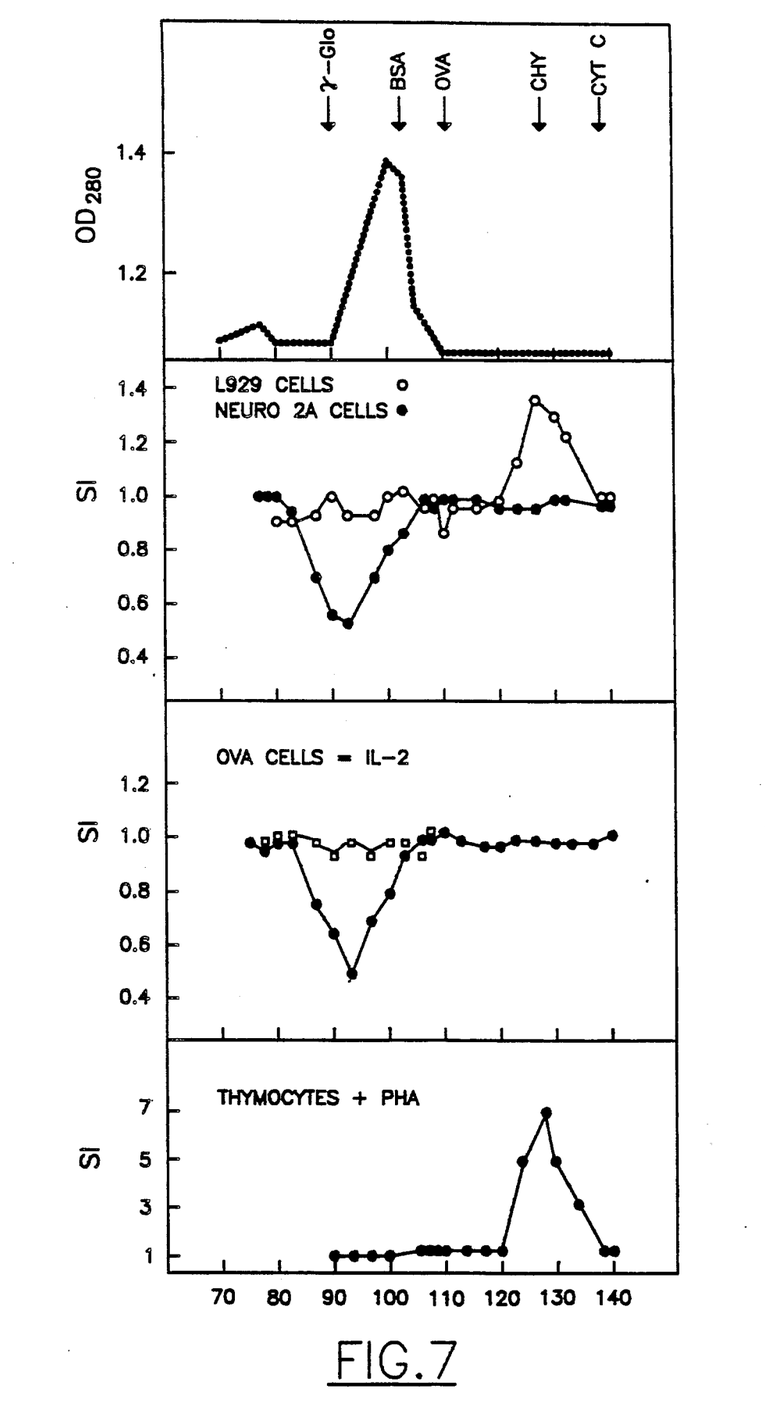
FIG. 7 is a series of graphs illustrating the stimulation index of 308 SN column fractions on various cells.

These results are summarized in FIG. 7 whereby the upper table shows the calibration run. Results are given as stimulation index (SI) comparing proliferation of cells treated with column fractions to cells treated with medium control. Results of serum-free control medium fractionated on a Sephacryl S-200 column are shown on OVA cells treated with IL 2 (□—□).

The peak of the inhibitory activity on neuroblasts and OVA cells was eluted from the column at the identical position, with an apparent m.w. of 97.000 (FIG. 7). Sephacryl S-200 fractions of a medium control consisting of DMEM (FIG. 7) and a medium control supplemented with 10% FCS (data not shown) had no inhibitory effects on the growth of OVA cells stimulated with IL 2. Furthermore, no inhibitory effect was observed when testing 308 SN fractions on fibroblasts. In fact, the growth of fibroblasts but not of neuroblasts or of IL 2-treated OVA cells was augmented by fractions that exhibit an apparent m.w. of around 22.000. These fractions were identified to additionally stimulate the PHA response of mouse thymocytes (FIG. 7) but to have no effect on the growth of OVA cells cultured in the absence of IL 2: the incorporation of $^3$H-Tdr by OVA cells was 284±72 and in the presence of IL 2 (final dilution 1/10) was 62038±2981. When OVA cells were treated with 308 fractions eluting from the column between m.w. 150.000 and 10.000, no proliferation of the OVA cells was observed, with cpm values never exceeding 500. This indicates the absence of IL 2 in 308 fractions including those that were found to augment the PHA response of thymocytes.

EXAMPLE 13

Figure 8:
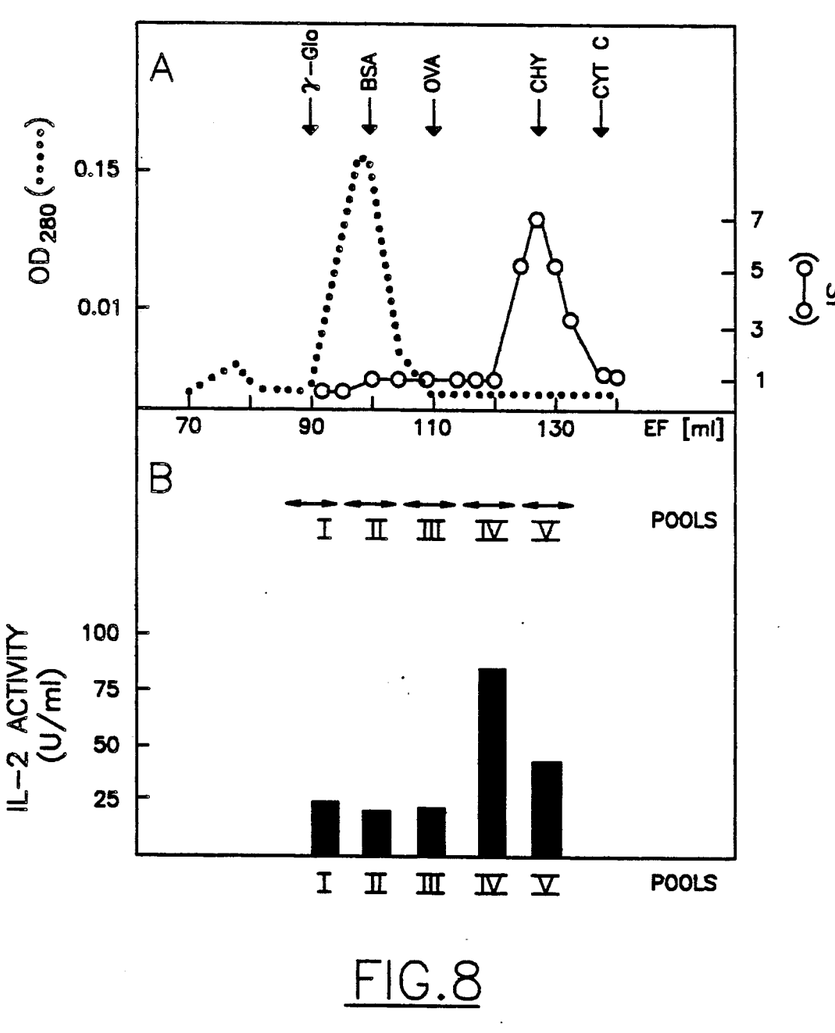
FIG. 8A is a graph illustrating the stimulation index and the response of thymocytes treated with 308 SN column fractions.
FIG. 8B illustrates the release of IL-2 by spleen cells exposed to pooled fractions of 308 SN column fractions.

Pools of chromatographed fractions of the 308 SN were assayed for their ability to enhance the release of IL 2 by spleen cells treated with suboptimal doses of Con A. and the results summarized in FIG. 8.

In FIG. 8 A fractions were assayed for their capacity to augment the PHA response of thymocytes: data are given as stimulation index (SI) comparing the PHA response of thymocytes treated with column fractions to untreated thymocytes. EF, effluent volume (ml). In B, pooled fractions (pool I to V) were concentrated 10× on YMB membranes and were tested for their ability to enhance the release of IL 2 by spleen cells (5×10$^6$/ml). After 44 hr the spleen cell SN were harveated, and the IL 2 activity was assayed on OVA cells. The activity in test samples was transformed into units as described in reference 13.

Activity =

$$\frac{\text{Reciprocal titer of test sample at 30\% of maximal standard cpm}}{\text{Reciprocal titer at 30\% of maximal standard cpm}}$$

In the absence of pooled fractions of 308 SN the amount of IL 2 released by spleen cells treated with Con A (0.5 μg/ml) was 21 U/ml: upon treatment with optimal doses of Con A (5 μg/ml the IL 2 content measured was 97 U/ml.

Compared with Con A alone, pool I to III neither stimulates nor inhibited the release of IL 2 (FIG. 8). However, with fraction pool IV and V the increase of the amount of IL 2 released was 3.5- and 1.6-fold, respectively (FIG. 8). Thus the capacity to enhance the release of IL 2 by spleen cells appears to be associated with fractions augmenting the PHA response of thymocytes.

In addition to inhibiting neuroblast growth, the 308 fractions were found to induce the outgrowth of neurites of Neuro 2A cells: 66% of Neuro 2A cells treated with fraction 93 (peak inhibitory fraction on neuroblast growth) showed cell processes, whereas the corresponding values in cultures treated with control fractions (fraction 112) or control medium were 21 and 22%, respectively.

As evidenced in the previous examples the immunosuppressant factor according to the invention is indicated for use in the treatment of diseases and conditions where suppression of the body's immune response is desired. Thus use in connection with transplant operations to prevent rejection is indicated. Examples of diseases where suppressions body's immune systems is indicated include the so-called auto-immune diseases.

For such use as daily dosage of about 10 to 2000 μg e.g. 200 to 1000 μg per patient is typically indicated.

The factor according to the invention can be employed in mixed form as purified supernatant from appropriate glioblastoma cell lines or in fractionated and purified form as hereinbefore described.

It can be got up in suitable form for administration in a manner conventional for substances of this nature in accordance with the condition to be treated. It can thus be injected intravenously in a suitable pharmacological carrier.

TABLE IV

| | EVALUATION OF ADSORBENTS FOR CHROMATOGRAPHY OF T-CELL SUPPRESSOR FACTOR | | | | | | |
|---|---|---|---|---|---|---|---|
| | G-TsF activity | | Total protein | | | | |
| Adsorbent | free$^a$ (Units) | bound$^b$ (Units) | free$^a$ (mg) | bound$^b$ (mg) | Adsorption | Desorption | pH |
| Hydroxyapatite | 16 | 74 | 0.2 | 1.7 | 0.01M tris-HCl 0.5M NaCl | 0.4M Na-phosphate | 7.5 |
| Blue-Affigel | 23 | 61 | 1.2 | 1.0 | 0.01M Tris-HCl | 2.0M NaCl | 7.5 |
| Phenyl-Sepharose | 32 | 51 | 0.9 | 0.7 | 0.25M Na-phosphate | 80% ethylene glycol | 7.5 |
| DEAE-Cellulose | 29 | 67 | 0.1 | 2.0 | 0.01M Tris HCl | 1.0M NaCl | 8.0 |
| DEAE-Cellulose | 45 | 43 | 0.2 | 1.8 | 0.01M Na-Hepes | 1.0M NaCl | 6.4 |

TABLE IV-continued
EVALUATION OF ADSORBENTS FOR CHROMATOGRAPHY OF T-CELL SUPPRESSOR FACTOR

| Adsorbent | G-TsF activity free[a] (Units) | G-TsF activity bound[b] (Units) | Total protein free[a] (mg) | Total protein bound[b] (mg) | Adsorption | Desorption | pH |
|---|---|---|---|---|---|---|---|
| Heparin-Affigel | 55 | 50 | 1.8 | 0.8 | 0.01M Tris-HCl | 1.0M NaCl | 7.5 |
| CM-Cellulose ConA-Sepharose Protein A-Sepharose | >80 | <20 | >2 | <0.5 | | | |

[a]After having equilibrated each adsorbent with 100 units of G-TsF (2.5 mg total protein) under the adsorption conditions listed here, the G-TsF activity and total protein remaining in solution were measured.
[b]G-TsF activity and total protein bound to the column were determined after desorption under the conditions listed here.

TABLE V
SUMMARY OF G-TsF PURIFICATION

| Step | | Volume (ml) | G-TsF activity[a] yeald (units) | G-TsF activity[a] yeald (%) | Protein[b] (mg) | Specific activity (units/mg) | Purification factor |
|---|---|---|---|---|---|---|---|
| | Crude 308 supernatant | 150 | 13800 | — | 360 | 38 | — |
| 1 | Amicon-concentrate | 50 | 13500 | 98 | 350 | 38 | 1 |
| 2 | Blue-Affigel 1.0–1.5M NaCl eluate | 70 | 7600 | 55 | 42 | 180 | 5 |
| 3 | Hydroxyapatite, 0.25–0.35M Na phosphate eluate | 22 | 6800 | 49 | 0.10 | 70000 | 1900 |
| 4 | Ultrogel AcA 54 | 75 | 6250 | 45 | 0.08 | 75000 | 2000 |

[a]Determined by ConA/thymocyte assay (see Material and Methods)
[b]Determined by amidoblack assay

TABLE VI
INACTIVATION OF G-TsF BY TRYPTIC PROTEOLYSIS

| Treatment | G-TsF activity Units/ml | G-TsF activity % of control |
|---|---|---|
| Control[a] | 164 | 100 |
| TPCK-trypsin 40 µg/ml, 1 hr, 37° C. | 42 | 26 |
| Immobilized RNase, 1 hr, 37° C. | 62 | 38 |
| Immobilized Trypsin, 1 hr, 37° C. | 4 | 2 |

[a]TPCK-trypsin added at the end of the incubation period

I claim:

1. An immunosuppressant factor composition, characterized by:
   a) inhibiting the incorporation of tritiated thymidine into murine thymocytes stimulated with Concanavalin A or phytohaemaglutinin in the presence of IL-2,
   b) inhibiting the proliferation of IL-2 dependent T cell clones,
   c) suppressing the growth of neuroblasts but not fibroblasts,
   d) inhibiting the generation of cytotoxic T cells in the allogenic mixed lymphocyte reaction,
   e) inhibiting the proliferation of haptenspecific cytotoxic T cells in the presence of haptenated stimulator,
   f) inhibiting the proliferative response of thymocytes to concanavalin A, and
   g) having a specific activity of at least 70,000 units/mg. in the ConA/thymocyte assay.

2. A composition according to claim 1 having a specific activity of at least 75,000 units/mg. in the ConA/thymocyte assay.

3. A composition according to claim 1 in which the immunosuppressant factor has a molecular weight of about 97,000 daltons.